United States Patent [19]

Hill et al.

[11] 4,166,695
[45] Sep. 4, 1979

[54] METHOD AND APPARATUS FOR MEASURING RETINAL BLOOD FLOW

[75] Inventors: David W. Hill, London; Edward R. Pike, Malvern, both of England

[73] Assignee: National Research Development Corporation, London, England

[21] Appl. No.: 782,510

[22] Filed: Mar. 29, 1977

[30] Foreign Application Priority Data

Apr. 1, 1976 [GB] United Kingdom ............... 13132/76

[51] Int. Cl.² .......................................... G01B 11/26
[52] U.S. Cl. ..................................... 356/28; 351/16; 356/39; 128/691; 128/745
[58] Field of Search ............... 356/103, 39, 28; 351/6, 351/7, 16; 128/2 T, 2.05 F

[56] References Cited

U.S. PATENT DOCUMENTS

| 3,137,756 | 6/1964 | Gunther et al. | 356/1 |
| 3,373,441 | 3/1968 | Zadig | 356/28 |
| 3,417,754 | 12/1968 | Smart | 351/16 |
| 3,487,835 | 1/1970 | Koester et al. | 351/16 |
| 3,503,682 | 3/1970 | Botcherby | 356/4 |
| 3,511,227 | 5/1970 | Johnson | 356/39 |

FOREIGN PATENT DOCUMENTS

| 1349365 | 4/1974 | United Kingdom | 356/28 |
| 1383158 | 2/1975 | United Kingdom | 128/2 T |

OTHER PUBLICATIONS

Tanaka et al., *Science;* vol. 186; Nov. 29, 1974; p. 830.
Riva et al., *Investigative Ophthalmology*, vol. 11, No. 11, p. 936, Nov. 1972.

*Primary Examiner*—S. C. Buczinski
*Attorney, Agent, or Firm*—Cushman, Darby & Cushman

[57] ABSTRACT

Blood flow in retinal blood vessels is measured by directing laser radiation along an optical path into the eye and onto a blood vessel. Laser radiation reflected off moving blood corpuscles is directed back along the optical path and into a detector. This reflected laser radiation is mixed with a proportion of the original laser signal to determine the doppler shift produced by the moving blood corpuscles and hence blood velocity.

8 Claims, 4 Drawing Figures

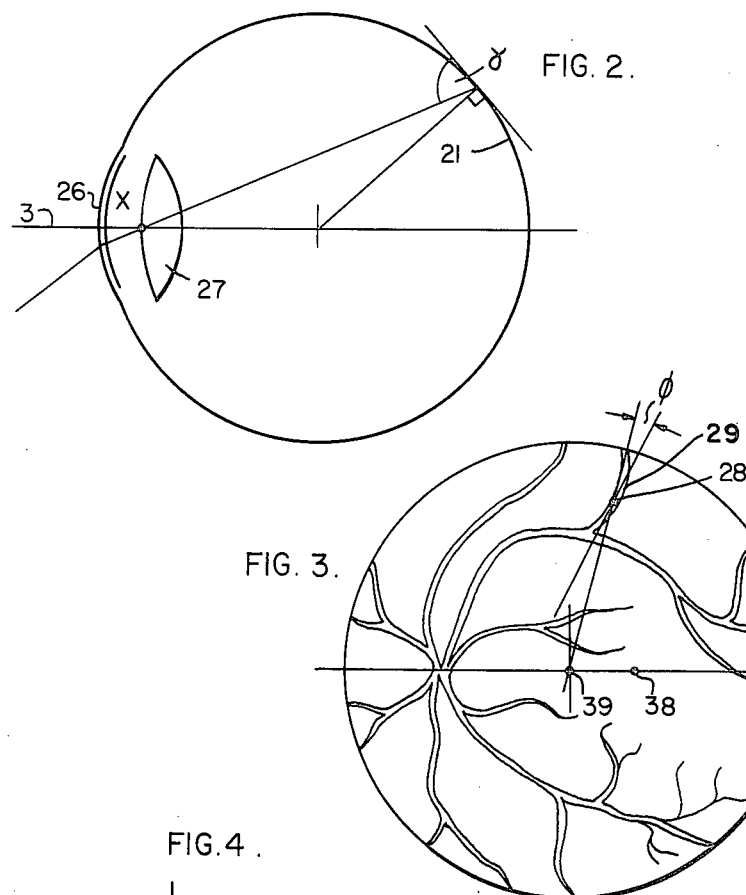
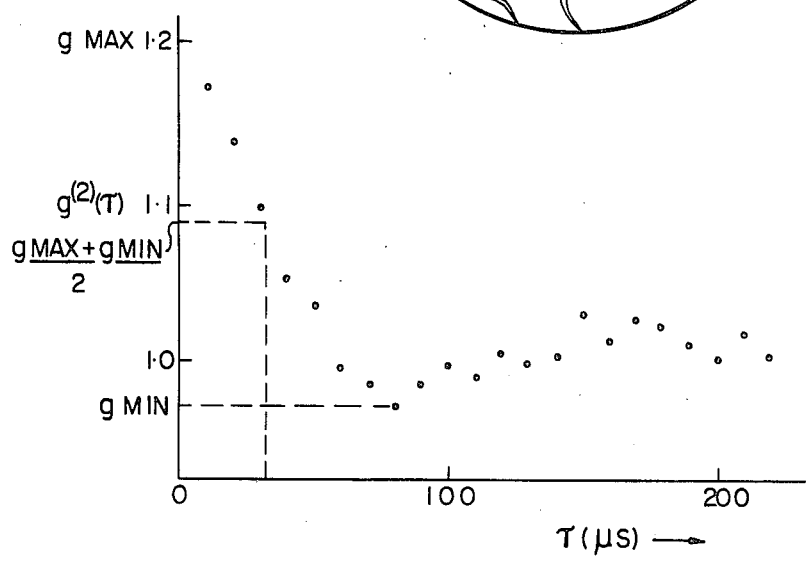

METHOD AND APPARATUS FOR MEASURING RETINAL BLOOD FLOW

This invention relates to a method of and apparatus for measuring retinal blood flow by laser doppler velocimetry.

Laser doppler velocimetry is a technique which allows the measurement of flow velocity by measuring the Doppler shift given to a laser beam scattered from moving particles suspended in the flow. This shift can conveniently be measured by mixing (homodyning) the scattered light with a portion of the original laser beam on the cathode surface of a photodetector. At low light levels the response of the photo-detector is a train of discrete output pulses, each corresponding to the absorption of a single photon at the cathode. These pulses are emitted randomly in time if the incident light intensity is constant but when a doppler beat frequency is present, the pulses are rate-modulated at this frequency.

The extraction of the doppler frequency from such a train of pulses can be effected by digital photon correlation (see Pike, 1972 Journal of Physics, D, 5 L23). The photon correlation function is the Fourier transform of the spectrum of frequency in the incident light field.

Retinal blood flow has previously been measured using laser doppler velocimetry by placing a large contact lens on a patient's eye, directing a beam of laser radiation through the contact lens and measuring light scattered along a second path at an angle to the laser beam. Such a technique is described in Science, 29 Nov. 1974, vol. 186, pages 830 to 831, and Investigative Opthalmology, Vol. 11, pp 936–944, Nov., 1972. One drawback with this technique as applied to man is the necessity for the patient to use a comparatively large and uncomfortable contact lens. Another is that such a bistatic system is intrinsically difficult to maintain in alignment in the presence of small eye movements.

A number of other techniques exist for measuring retinal blood flow in man and in anaesthetized animals. In animal experimental work the foremost is cinefluorescein angiography, the recording of a dye bolus moving along the arteries. The methods applicable to human investigation are based on fluorescein angiography, all are necessarily invasive, involving the injection of dye, they are complicated, relatively inaccurate, and cannot be frequently repeated.

According to this invention a method of measuring retinal blood flow includes the steps of directing laser radiation along an optical path, locating an eye along the optical path, directing the laser radiation onto a retinal blood vessel, receiving light scattered by blood corpuscles back along the same optical path, and processing this light scattered by blood corpuscles to determine a doppler signal.

The eye may be positioned along the optical path at a position at which the laser radiation when at an angle to the optical axis passes through the anterior lens surface at its intercept with the optical axis i.e. the principal ray. Alternatively the laser radiation may pass through the intercept with a cornea surface.

The laser radiation may be a single beam of radiation, part of which is scattered by the blood corpuscles and directed back onto the detector to be mixed with part of the radiation not scattered by the moving corpuscles. This latter part of the radiation may be from non-moving parts of the eye such as the lens or cornea or blood vessel walls, and or an adjustable specular or non-specular reflector which is illuminated by a beam splitter in the optical path. Such a reflector allows adjustment of the intensity of the original signal frequency, i.e. the local oscillating signal, to obtain optimum signal to noise ratio on the detector.

Alternatively twin beams of converging laser radiation may be directed along the optical path to interact at a retinal blood vessel to form a set of interference fringes. Measurements of fluid flow through fringes is described in J. Physics, D 5 L23.

Apparatus for carrying out the method of this invention includes a laser for producing a beam of radiation, a polarising prism arranged to pass laser radiation of one plane of polarisation and to reflect another plane of polarisation, a detector for detecting laser radiation, a beam deflector for varying the angular direction of the laser radiation, means for focussing the laser beam into a person's eye, a beam splitter for passing radiation reflected from within an eye to the detector and for passing a proportion of this reflected radiation through a viewing eye-piece,, and a light source for providing general illumination of the fundus, whereby a beam of laser radiation may be directed along an optical path and onto retinal blood vessels, and radiation reflected by a blood vessel is directed back along the optical path and into the detector.

The invention will now be described with reference to the accompanying drawings in which:

FIG. 2 is a section through an eye;

FIG. 3 is a view of retinal blood vessels;

FIG. 4 shows a correlation function.

Figure 1:
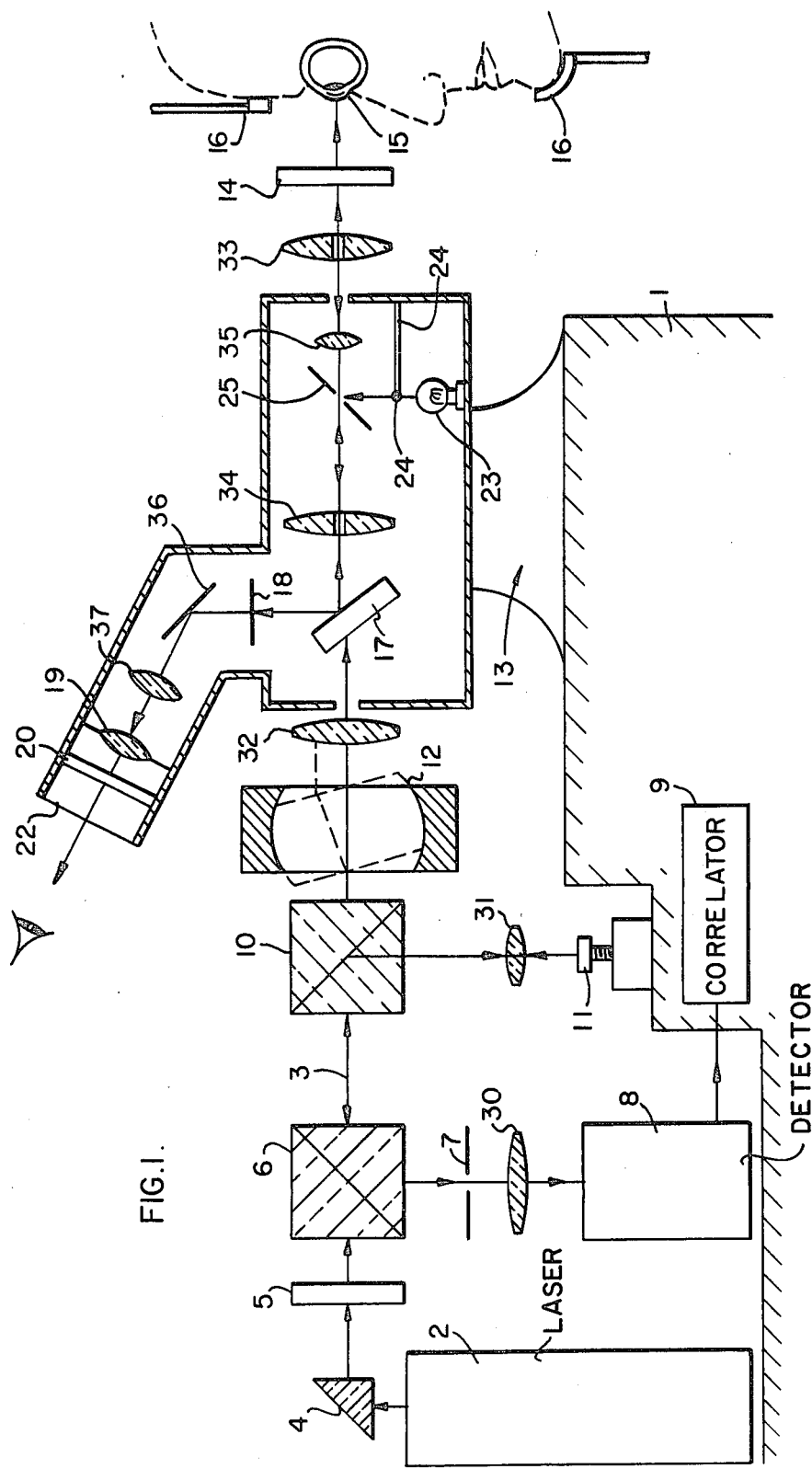
FIG. 1 is a diagrammatic view of apparatus for measuring retinal blood flow.

As shown in FIG. 1 the apparatus for measuring retinal blood flow comprises a table 1 which carries a 1 milliwatt $H_eN_e$ laser 2 arranged to pass a beam of laser radiation (attenuated to about 10 microwatt) along an optical path 3 into a patient's eye. The laser radiation is reflected from the laser 2 by a prism 4 and through variable attenuator 5 which reduces the laser radiation intensity to a safe value. From the attenuator 5 the radiation passes through a polarising prism 6 arranged to pass all the vertically polarised radiation from the laser 2 but reflect all returning horizontally polarised light through a variable aperture 7 and lens 30 into a photo detector and multiplier 8. Output of the photo multiplier 8 in the form of a train of descrete pulses is fed into a digital photon correlator 9 such as the correlator described in U.K. Pat. No. 1,290,336 (U.S. Pat. No. 3,842,252, Japanese Patent Application No. 24,806/70 and German Patent No. P 2014529) e.g. Precision Devices & Systems, Model K 7023. The aperture 7 is adjustable to exclude extraneous reflections and to optimise signal to noise ratio. Radiation from the laser 2 passes through the polarising prism 6 into a beam splitter 10 where a proportion is deflected through a lens 31 onto an adjustable non-specular reflector 11 and thence back through the beam splitter 10 and polarising prism 6 onto the photo detector 8 where it forms the local oscillator signal for homodyning with radiation scattered by a retinal blood vessel. The remainder of the laser radiation passes through a beam positioner 12, a lens 32, a fundus camera 13, a central hole in a lens 33 and quarter wave plate 14 into a patient's eye 15. The patient's position is kept steady by head and chin rests 16.

The fundus camera 13 is a standard camera and basically comprises a beam splitter 17 which passes the vertically polarised light from the laser 2 through lenses 34 and 35 to the eye 15 and splits returning horizontally polarised light. Most of this returning horizontally polarised light passes back towards the photo detector 8 but about 5% is reflected upwards through a reticule 18, reflected by a mirror 36 through a lens 37, an eye piece 19 and polariser 20 set to pass horizontally polarised light. The beam splitter 17 is coated to allow also most of the white light to be reflected upwards. The polariser 20 removes spurious reflections from lenses within the camera 13 whilst allowing observation of the position of the laser beam on the retina 21, FIG. 2. A further λ/4 plate may be used before the polariser to improve the rejection of spurious reflections. Above the polariser 20 is a cross wire sight 22 for use in measuring the angle of a blood vessel. Alternatively this may be sited within the viewing system. Inside the camera 13 is a light source 23 whose light is reflected by a mirror 25 with a central opening into the eye for general illumination of the fundus 21. An adjustable internal target 24 is focussed at infinity in the light path between light sources 23 and mirror 25 and is used by the patient to align the eye so that the optical pole 39 of the eye is along the optical path 3 of the fundus camera with the target 24 focussed along the visual axis of the eye 15 on to the fovea 38, FIG. 3. Alternatively an adjustable fixation lamp may be used with the second eye.

In operation a patient is positioned in front of the camera 13 and held steady by the head rests 16. The light 23 within the camera 13 is switched on to illuminate the fundus 21 and to enable the patient to align on the internal target 24 or external fixation lamp. The laser 2 is caused to emit vertically polarised light most of which after suitable attenuation is focussed into the eye 15. With the beam positioner 12 in its centre position, i.e. so that the laser beam is undeflected, the relative positions of equipment and eye are adjusted so that the reflection from cornea 26, lens 27 and retinal scattering from the far pole 39 of the optical axis of the eye all lie along the optic axis 3 of the equipment. This is achieved by aligning the four reflections from the surfaces of the cornea and lens (the Purkinje images) or by aligning the anterior corneal reflection with the laser beam placed at the previously determined optic pole 39 of the fundus. Alternatively the first and fourth Purkinje image (from the anterior cornea 26 surface and posterior lens 27 surface) can be aligned by lateral and rotational movement of the eye 15, relative to the camera 13, so that the observed larger first and smaller fourth Purkinje image are co-axial. These images may be of a spot of laser light or camera interior light reflected by the eye and focussed by the lens 33.

When using the so-called principal ray it is also necessary to have the eye a certain distance from the camera so that a deflected laser beam always passes through the anterior lens surface at its intercept with the optical axis, i.e. position X in FIG. 2. This is achieved by deflecting the laser beam and observing both the movement of the laser beam on the retina 21, which is seen as a small spot 28, FIG. 3, and the reflection of the laser beam from the lens 27 surface, which is seen as a spot moving in the opposite direction to the spot on the retina 21. The relative positions of eye and equipment are adjusted until both spots move an equal amount either side the optical axis; the eye is then correctly positioned.

Alternatively the position of the eye along the axis can be varied while making continuous movements of the beam positioner. The correct distance is achieved when the scattering observed from the laser beam passing through the lens 27 shows the correct paths being followed, that is, the entry point to the lens 27 does not vary as the beam positioner is moved. This observation is made directly at the eye itself not through the eye piece 19 of the fundus camera 13.

The beam positioner 12 is then moved until the laser spot 28 is incident on a blood vessel 29 whose blood flow is to be determined. It is necessary that the blood vessel has a radial component, FIG. 3, of blood flow. Corpuscles in the blood stream scatter the laser beam and this scattered light is returned through the camera 13, beam positioner 12, beam splitter 10 and polarising prism 6 to the photo detector 8 and mixed (homodyned) with light from the reflector 11 to produce a doppler signal which is then processed to show blood velocity.

The doppler angle is derived from tabulated values of the acceptance angle γ, FIG. 2, in the literature e.g. W. Lotmar, J. Opt. Soc. Am. 61 1522 71. for given angles of beam deflection obtained from the position of the beam positioner. Also the doppler angle is dependent upon the radial angle, φ (FIG. 3), of the blood vessel and this is measured by aligning the cross wires with the direction of the illuminated blood vessel at the point of illumination.

The radiation passes through the whole of the vessel and light is scattered by red corpuscles moving at different velocities, from near zero at the walls to the maximum value at the centre of the vessel. The received doppler signal is thus a sum of frequencies which, for a vessel narrow compared with the beam diameter, and an assumed parabolic flow profile results in a correlation function g(τ) of the form $$g(\tau) = \frac{\sin 2\pi f \tau}{2\pi f \tau} - \frac{1}{2} \left( \frac{\sin \pi f \tau}{\pi f \tau} \right)^2$$

where f is the maximum doppler frequency given by $$f = 2 \cos \gamma \cos \phi \; \sigma_{max}/\lambda$$

where $\sigma_{max}$ is the centre-line flow velocity and λ the light wavelength. The value of $\sigma_{max}$ can be recovered by suitable post correlation analysis. The average velocity for this profile is $\sigma_{max}/2$. A working approximation may be obtained by observing that the point at the half height of the first limb of the correlation function, $\tau_{\frac{1}{2}}$ (FIG. 4), lies close to $\frac{1}{3}f$, thus, $\sigma_{ave} \simeq \lambda/12 \; \tau_{\frac{1}{2}} \cos \gamma \cos \phi$. More complex expressions may be calculated for non-parabolic profiles and finite values of vessel-to-beam-diameter ratios.

We claim:

1. Apparatus for measuring retinal blood flow comprising a laser for producing a beam of radiation, means for directing a single beam of the laser radiation along an optical path into an eye and onto a retinal blood vessel, a detector for detecting laser radiation reflected from blood corpuscles within the blood vessel, and for producing a doppler output signal, means for directing laser radiation reflected by the eye into the detector, means for variably deflecting the laser radiation across the optical path to enable the desired part of the retinal blood vessels to be illuminated by the laser radiation and defining an acceptance angle, a light source for general illumination of the fundus of the eye, means for observing light and laser radiation reflected by the eye and for determining the angle of the blood vessel, the doppler angle of the blood vessel being determined from said acceptance angle and said angle of the blood vessel, whereby the laser radiation may be directed along the optical path and onto the retinal blood vessel and the laser radiation reflected from the blood vessel is reflected back along the optical path into the detector to determine the doppler shift of laser radiation and hence blood flow velocity from the value of the doppler output signal and from the doppler angle defined by said acceptance angle and said angle of blood vessel.

2. Apparatus according to claim 1 and comprising a beam splitter for directing a proportion of the laser radiation onto a reflector and thence back into the detector to form a signal for mixing with radiation scattered by the retinal blood vessel.

3. Apparatus according to claim 2 wherein means are provided for varying the amount of signal that is reflected back into the detector.

4. Apparatus according to claim 1 wherein the means for directing radiation into the detector includes a polarising prism which transmits one plane of polarisation and reflects an orthogonal plane of polarisation.

5. Apparatus according to claim 4 wherein the means for directing radiation into the detector comprises a quarter wave plate for changing the plane of polarisation reflected back along the optical path.

6. Apparatus according to claim 1 wherein the means for variably deflecting laser radiation comprises a plate of transparent material whose surfaces are adjustable about a plane normal to the optical path.

7. Apparatus according to claim 1 and comprising an adjustable target and reflecting surfaces for reflecting an image of the target into the eye whereby the eye can be positioned with the optic axis along the optical path of the apparatus.

8. Apparatus according to claim 7 wherein the means for observing radiation reflected by the eye includes a beam splitter for reflecting a part of light reflected by the eye through a viewing eye piece means.

* * * * *